US009603638B2

(12) United States Patent
Donner et al.

(10) Patent No.: US 9,603,638 B2
(45) Date of Patent: Mar. 28, 2017

(54) SPINAL STABILIZATION SYSTEM

(71) Applicant: JCBD, LLC, Fort Collins, CO (US)

(72) Inventors: Edward Jeffrey Donner, Fort Collins, CO (US); Christopher Thomas Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 0 days.

(21) Appl. No.: 15/332,947

(22) Filed: Oct. 24, 2016

(65) Prior Publication Data

US 2017/0035467 A1 Feb. 9, 2017

Related U.S. Application Data

(63) Continuation of application No. 14/209,138, filed on Mar. 13, 2014, now Pat. No. 9,510,872.

(60) Provisional application No. 61/794,543, filed on Mar. 15, 2013.

(51) Int. Cl.
*A61B 17/70* (2006.01)

(52) U.S. Cl.
CPC ...... *A61B 17/7071* (2013.01); *A61B 17/7026* (2013.01); *A61B 17/7043* (2013.01); *A61B 17/7067* (2013.01)

(58) Field of Classification Search
CPC .................. A61B 17/7062; A61B 17/7071
See application file for complete search history.

(56) References Cited

U.S. PATENT DOCUMENTS

| 5,415,661 | A * | 5/1995 | Holmes | A61B 17/7062 606/255 |
| 5,645,599 | A * | 7/1997 | Samani | A61B 17/7062 606/248 |
| 6,565,605 | B2 * | 5/2003 | Goble | A61F 2/4405 606/248 |
| 7,699,873 | B2 * | 4/2010 | Stevenson | A61B 17/7067 606/248 |
| 8,262,697 | B2 * | 9/2012 | Kirschman | A61B 17/7058 606/248 |
| 8,568,453 | B2 * | 10/2013 | Abdou | A61B 17/7068 606/248 |
| 8,801,757 | B2 * | 8/2014 | Abdou | A61B 17/7067 606/246 |
| 2002/0116000 | A1 * | 8/2002 | Zucherman | A61K 31/37 606/249 |
| 2002/0147449 | A1 * | 10/2002 | Yun | A61B 17/7062 606/249 |

(Continued)

*Primary Examiner* — Ellen C Hammond
*Assistant Examiner* — Stuart S Bray
(74) *Attorney, Agent, or Firm* — Glenn H. Lenzen; Dietze and Davis, P.C.

(57) ABSTRACT

A spinal stabilization system and method are provided for treating a patient's spinal column, for maintaining preselected spacing and movement between adjacent vertebrae in a spinal column, and for providing overall stability thereto. The system includes interlaminar members positioned in the spaces intermediate a first vertebra and the vertebrae positioned immediately above and immediately below and adjacent to the first vertebra. The interlaminar members are operatively connected to one another by an adjustable support structure and cooperate therewith to maintain the preselected spacing between adjacent vertebrae and to provide overall stability to the spinal column.

20 Claims, 13 Drawing Sheets

(56) References Cited

U.S. PATENT DOCUMENTS

| | | | |
|---|---|---|---|
| 2003/0171750 A1* | 9/2003 | Chin | A61F 2/4405 606/247 |
| 2004/0117017 A1* | 6/2004 | Pasquet | A61B 17/7062 623/17.11 |
| 2005/0033434 A1* | 2/2005 | Berry | A61B 17/7064 623/17.14 |
| 2005/0131409 A1* | 6/2005 | Chervitz | A61F 2/4611 606/247 |
| 2006/0142759 A1* | 6/2006 | Arnin | A61B 17/7043 623/17.14 |
| 2006/0217718 A1* | 9/2006 | Chervitz | A61B 17/7064 606/247 |
| 2006/0224159 A1* | 10/2006 | Anderson | A61B 17/7062 606/248 |
| 2006/0241601 A1* | 10/2006 | Trautwein | A61B 17/7049 606/248 |
| 2006/0241642 A1* | 10/2006 | Arnin | A61F 2/4611 606/90 |
| 2006/0241757 A1* | 10/2006 | Anderson | A61B 17/7062 623/17.11 |
| 2007/0162000 A1* | 7/2007 | Perkins | A61B 17/7062 606/249 |
| 2008/0177264 A1* | 7/2008 | Alamin | A61B 17/7065 606/74 |
| 2008/0177326 A1* | 7/2008 | Thompson | A61B 17/7047 606/277 |
| 2008/0228225 A1* | 9/2008 | Trautwein | A61B 17/1606 606/246 |
| 2008/0234733 A1* | 9/2008 | Scrantz | A61B 17/7062 606/246 |
| 2008/0269904 A1* | 10/2008 | Voorhies | A61B 17/7026 606/86 A |
| 2008/0306525 A1* | 12/2008 | Mitchell | A61B 17/7005 606/246 |
| 2009/0018662 A1* | 1/2009 | Pasquet | A61B 17/7008 623/17.16 |
| 2009/0024169 A1* | 1/2009 | Triplett | A61B 17/1757 606/248 |
| 2009/0138048 A1* | 5/2009 | Baccelli | A61B 17/8869 606/263 |
| 2009/0149885 A1* | 6/2009 | Durward | A61B 17/7067 606/246 |
| 2009/0216276 A1* | 8/2009 | Pasquet | A61B 17/7043 606/249 |
| 2009/0259261 A1* | 10/2009 | Reiley | A61B 17/8897 606/329 |
| 2009/0264929 A1* | 10/2009 | Alamin | A61B 17/7062 606/248 |
| 2009/0270920 A1* | 10/2009 | Douget | A61B 17/7055 606/254 |
| 2009/0292314 A1* | 11/2009 | Mangione | A61B 17/7062 606/249 |
| 2010/0010496 A1* | 1/2010 | Isaza | A61B 17/1742 606/96 |
| 2010/0069965 A1* | 3/2010 | Abdou | A61B 17/7064 606/279 |
| 2011/0034957 A1* | 2/2011 | Biedermann | A61B 17/7035 606/305 |
| 2011/0071568 A1* | 3/2011 | Ginn | A61B 17/7062 606/249 |
| 2011/0106163 A1* | 5/2011 | Hochschuler | A61B 17/7062 606/264 |
| 2011/0160772 A1* | 6/2011 | Arcenio | A61B 17/7053 606/248 |
| 2011/0218571 A1* | 9/2011 | Attia | A61B 17/7062 606/248 |
| 2012/0065683 A1* | 3/2012 | Kuo | A61B 17/7062 606/248 |
| 2012/0109198 A1* | 5/2012 | Dryer | A61B 17/7062 606/248 |
| 2012/0109202 A1* | 5/2012 | Kretzer | A61B 17/7049 606/248 |
| 2012/0130427 A1* | 5/2012 | Hoffman | A61B 17/7055 606/248 |
| 2012/0136390 A1* | 5/2012 | Butler | A61B 17/7067 606/248 |
| 2012/0150228 A1* | 6/2012 | Zappacosta | A61B 17/7068 606/248 |
| 2012/0158060 A1* | 6/2012 | Abrahams | A61B 17/7052 606/248 |
| 2012/0184997 A1* | 7/2012 | Simonson | A61B 17/7007 606/265 |
| 2012/0215262 A1* | 8/2012 | Culbert | A61B 17/1606 606/279 |
| 2012/0226312 A1* | 9/2012 | Thalgott | A61B 17/7062 606/246 |
| 2012/0226314 A1* | 9/2012 | Chin | A61L 27/425 606/249 |
| 2012/0259370 A1* | 10/2012 | Vaidya | A61B 17/6433 606/281 |
| 2012/0296428 A1* | 11/2012 | Donner | A61F 2/30988 623/17.11 |
| 2013/0023933 A1* | 1/2013 | Haas | A61B 17/7065 606/248 |
| 2013/0030467 A1* | 1/2013 | Karas | A61B 17/686 606/248 |
| 2013/0035727 A1* | 2/2013 | Datta | A61B 17/7055 606/279 |
| 2013/0053854 A1* | 2/2013 | Schoenefeld | A61B 17/1757 606/87 |
| 2013/0072979 A1* | 3/2013 | Butler | A61B 17/7068 606/248 |
| 2013/0296939 A1* | 11/2013 | Perkins | A61B 17/7068 606/249 |
| 2014/0052183 A1* | 2/2014 | Freese | A61B 17/0401 606/248 |
| 2014/0316467 A1* | 10/2014 | Siegal | A61B 17/7062 606/249 |
| 2015/0012040 A1* | 1/2015 | Agarwal | A61B 17/7068 606/248 |
| 2015/0182263 A1* | 7/2015 | Donner | A61B 17/7067 606/248 |

\* cited by examiner

SPINAL STABILIZATION SYSTEM

CROSS-REFERENCE TO RELATED APPLICATIONS

This application is a continuation of U.S. patent application Ser. No. 14/209,138, filed Mar. 13, 2014, which claims the benefit of U.S. Provisional Application No. 61/794,543, filed Mar. 15, 2013. The entire disclosures of which are incorporated herein by reference.

FIELD OF THE INVENTION

The present invention relates generally to the field of medical apparatus and methods for using the same. More specifically, the present invention relates to systems and methods for treating spinal conditions, and specifically for systems for stabilizing vertebrae in the spinal column. More specifically, the present invention relates to interlaminar vertebral stabilization devices for placement between adjacent vertebra and including supporting devices for stabilization of the vertebral segments above and below the vertebra being treated.

BACKGROUND OF THE INVENTION

Injury to and/or diseases of the spine frequently result in damage to or abnormalities in the vertebrae, the intervertebral discs, the facet joints and to the connective tissue and ligaments around the spine. Such damage or abnormalities may result in spinal instability causing misalignment of the vertebral column and wear of the intervertebral discs and vertebral bony surfaces, a chronic and progressive deterioration which typically results in severe pain, loss or restriction of motion, and eventually, loss of mobility of the individual suffering from the condition.

One treatment option for addressing spinal disorders is via surgical intervention and the placement of fusion, stabilization and/or repair devices on or adjacent to the spine or between adjacent vertebrae. Certain surgical procedures are irreversible, for example, fusion techniques using bone grafts or synthetic implants to fuse vertebra, and may also significantly alter vertebral range of motion. Other procedures, for example procedures for installing spinal implants or pedicle screw systems for fixating two or more vertebrae, are intricate, time consuming and highly invasive. Alternative solutions include the insertion of interspinous or intralaminar spacers in the space between adjacent vertebrae to control relative motion between and to stabilize the two vertebrae. However, the stabilization does not extend above or below the insertion point, leaving the remaining portions of the spinal column subject to unstable motion and the potential damage resulting therefrom.

Various prior art systems have attempted to address the problems described above. U.S. Pat. No. 5,645,599 issued to Samani on Jul. 8, 1997 (the '599 patent), discloses an interspinal implant device having a generally u-shaped, spring-like configuration for insertion between the spinal processes of adjacent vertebrae. Samani's device includes opposing pairs of upwardly and downwardly extending brackets adapted to be secured to the spinal process, thereby providing for flexible positioning of the adjacent vertebrae. However, the apparatus of the '599 patent does not attribute to the overall stability of the spinal column; its effect being limited to the two specific vertebrae to which it is attached. It is also difficult to attach multiple devices configured in accordance with Samani's disclosure at adjacent segments due to interference of the bracket portions.

Hochschuler et al disclose various intra-laminar stabilization systems in U. S. Patent Application Publication No. US 2009/0204150 published on Aug. 13, 2009 (the '150 publication), and in U. S. Patent Application Publication No. US 2011/0106163 published on May 5, 2011 (the '163 publication). The '150 publication discloses a pair of oppositely disposed hook members that are translationally positioned on a rod and adapted to engage the laminar regions of adjacent vertebra and maintain a preselected spacing there between. However, the apparatus of the '150 publication does not stabilize other vertebrae in the spinal column, its effect being limited to the two adjacent vertebrae which it engages.

The Hochschuler et al. '163 publication discloses an interlaminar stabilizing system which includes a structure adapted to be disposed between two adjacent vertebrae as described above with respect to the apparatus of the '150 publication. The '163 structure further includes a support structure which is secured to the second vertebra to further restrict the interval spacing between the adjacent vertebrae. However, the system of the '163 disclosure also does not stabilize the vertebrae in the remaining portions of the spinal column for the reasons set forth above.

Moreover, none of the known prior art systems address the problem of "transition syndrome" or "adjacent segment disease" associated with fusion of adjacent vertebrae. In fusion, if a motion segment is eliminated via fusion, the unfused adjacent segments above and below the fused vertebrae take up and bear the additional forces induced by bending and rotational movement of the spine, which may result in so-called "transition syndrome" over the long term. In addition, none of the prior art systems provide for augmenting previously installed spinal hardware to enhance stability, adjust intervertebral distraction, and so forth.

Accordingly, a need exists for an improved spinal stabilization system which provides both flexibility and stability to the spinal column and which addresses the combination of problems not solved by the prior art.

SUMMARY OF THE INVENTION

The stated problems and other needs in the art as apparent from the foregoing background may be addressed in accordance with the systems and methods of the present invention as set forth in various embodiments disclosed herein.

In an embodiment, an improved spinal stabilization system is provided for maintaining preselected spacing and movement between adjacent vertebrae and also for providing overall stability to the spinal column.

In one embodiment, a spinal stabilization system is provided which includes at least one interlaminar member adapted to be inserted between two adjacent vertebrae and a stabilizing structure for stabilizing the vertebrae at least one layer above and below the two adjacent vertebrae.

In another embodiment, a spinal stabilization system is provided which includes a blocking member to limit movement of adjacent vertebrae to prevent narrowing of the spinal canal and nerve compression.

In yet another embodiment, a spinal stabilization system is provided which includes at least one adjustable cross-linking member to enhance stability of the spine.

In still another embodiment, a method for treating a patient's spinal column is disclosed employing at least one of the embodiments of the spinal stabilization system of the present invention.

These and other features of the present invention will be apparent from the accompanying description of the invention, diagrams and supplemental supporting materials provided herein.

DESCRIPTION OF THE INVENTION

It should be noted that the present description is by way of illustration only, and that the concepts and examples presented herein are not limited to use or application with any single system or methodology. Hence, while the details of the system and methods described herein are for the convenience of illustration and explanation with respect to the exemplary embodiments, the principles disclosed may be applied to other types of spinal stabilization systems without departing from the scope of the present invention.

Figure 1:
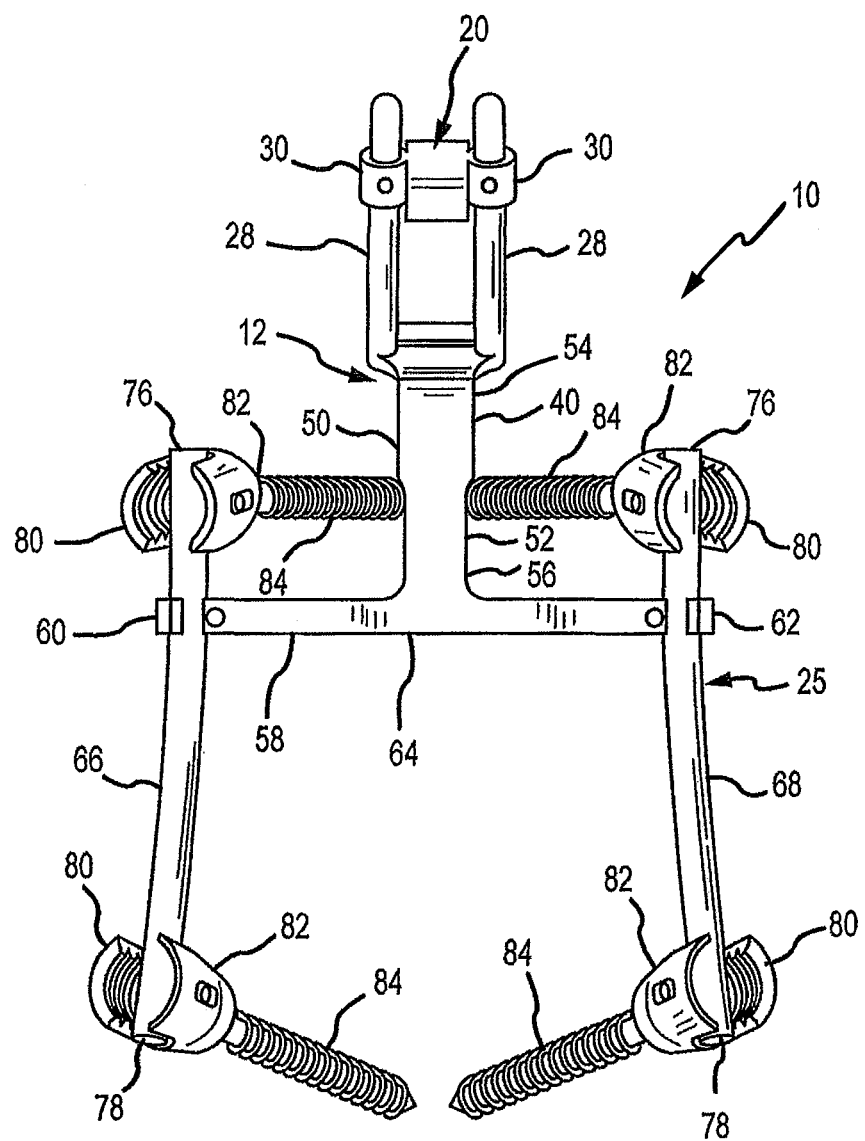
FIG. 1 is a front plan view of a spinal stabilization system of the present invention.
Figure 2:
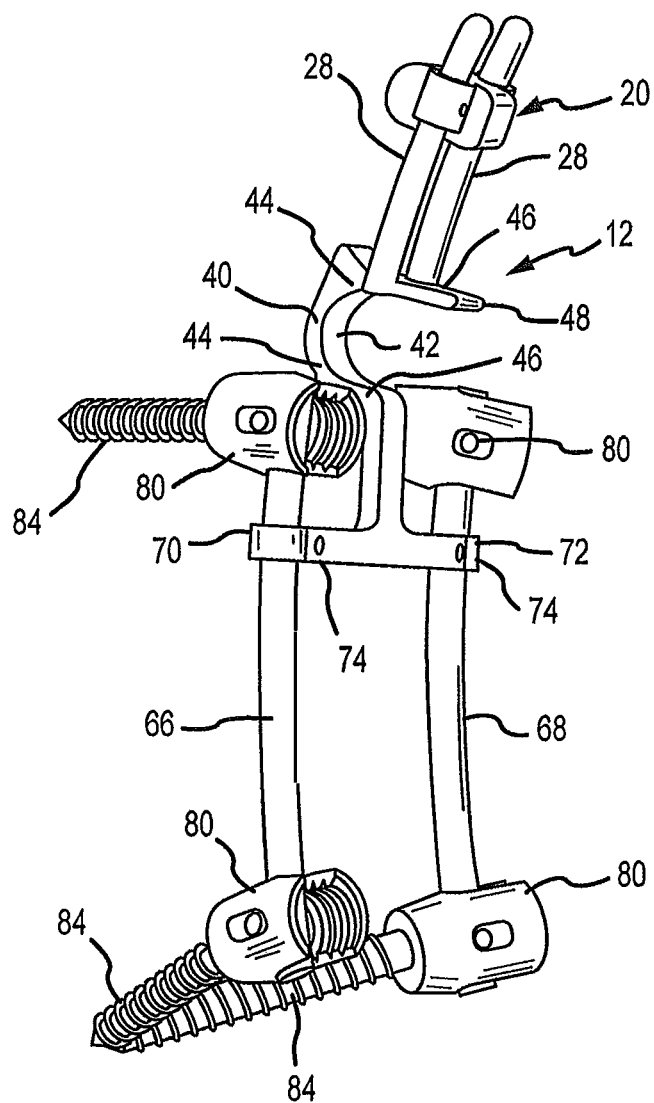
FIG. 2 is a side perspective view of a spinal stabilization system of the present invention.
Figure 3:
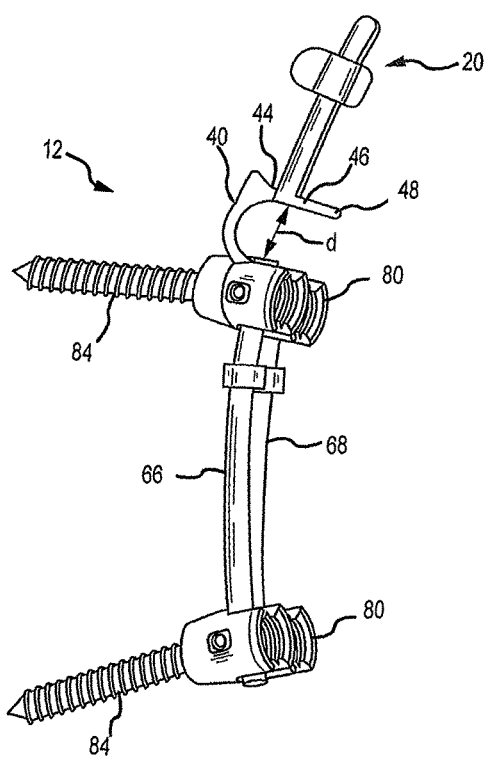
FIG. 3 is a side plan view of a spinal stabilization system of the present invention.
Figure 4:
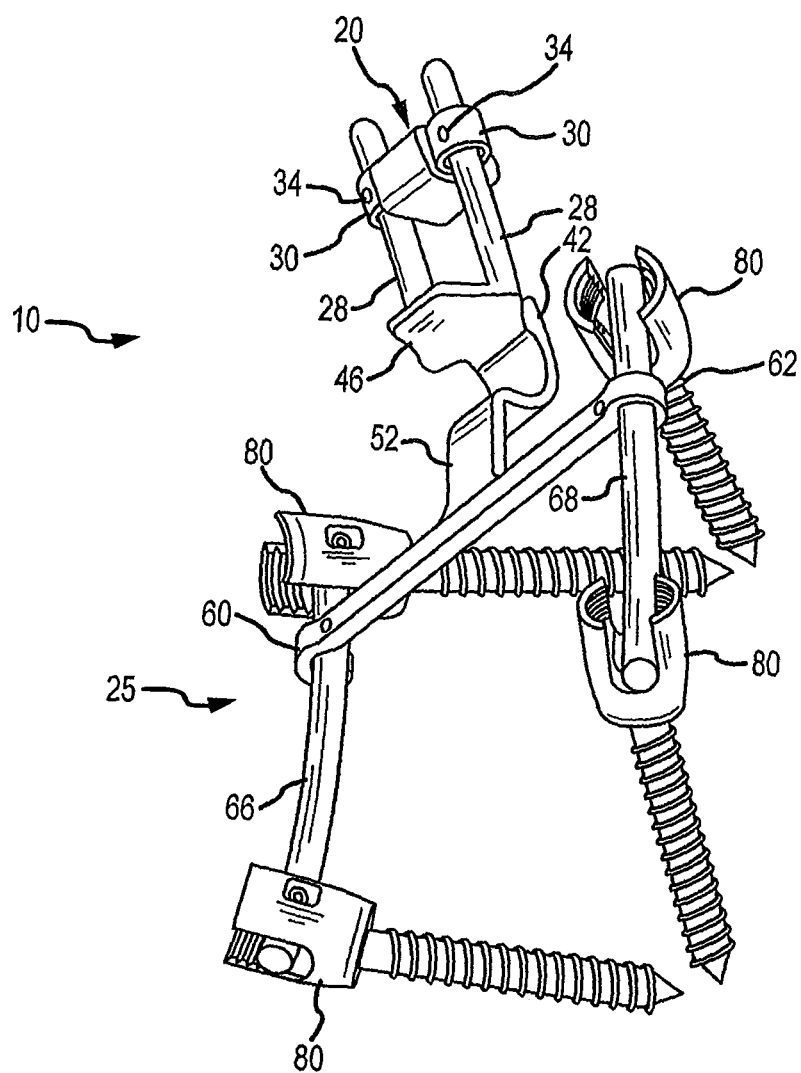
FIG. 4 is a bottom perspective view of a spinal stabilization system of the present invention.
Figure 5:
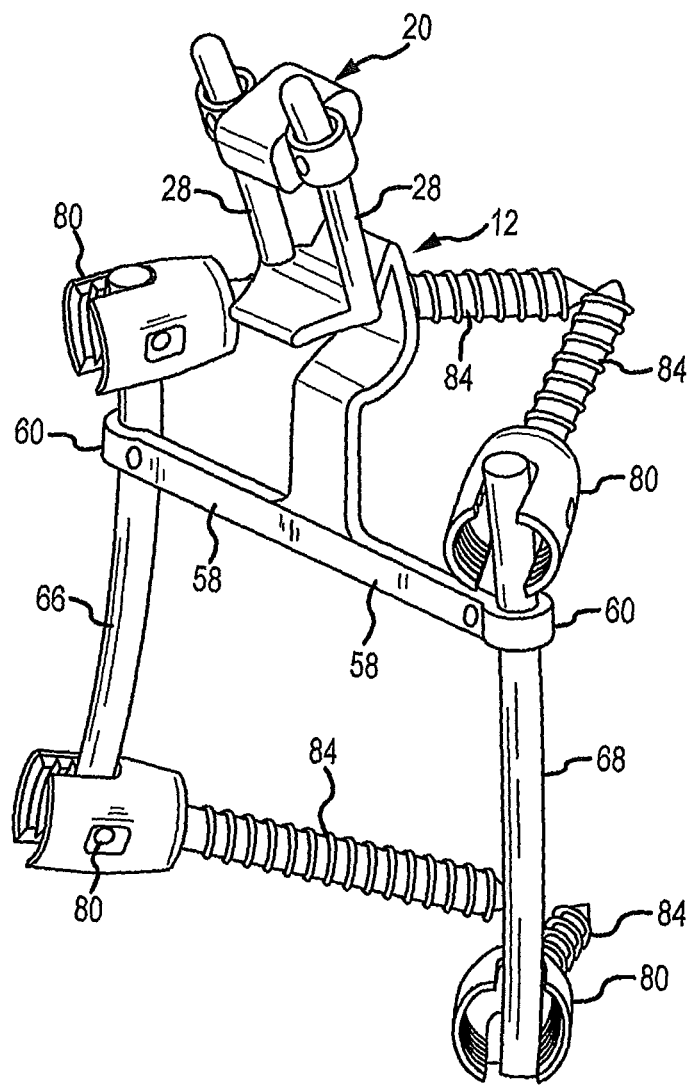
FIG. 5 is a top perspective view of a spinal stabilization system of the present invention.

Referring now to FIG. 1, a spinal stabilization system according to an embodiment of the present invention is shown generally at 10 (which for purposes of brevity will be referred to herein as "the system"). The system includes a first interlaminar member 12 adapted to be positioned between adjacent vertebra in a spinal column. As shown in greater detail in FIGS. 6 and 7, the interlaminar member 12 is shown positioned between a first vertebra 14 and a second adjacent vertebra 16 in a spinal column 18.

The system further includes a second interlaminar member 20 adapted to be positioned between the second vertebra 16 and a third vertebra 22 in the spinal column 18. Both the first and second interlaminar members are operatively connected to a support structure shown generally at numeral 25 in FIG. 1. By way of example, in the embodiment shown, the support structure and the first interlaminar member are integrally formed from a single piece of material such as titanium or stainless steel suitable for use as a medical implant device. However, it is to be understood that other means for connecting the interlaminar device to the support structure such as hinges, pins, threaded fasteners and the like may also be used without departing from the scope of the invention.

Figure 9:
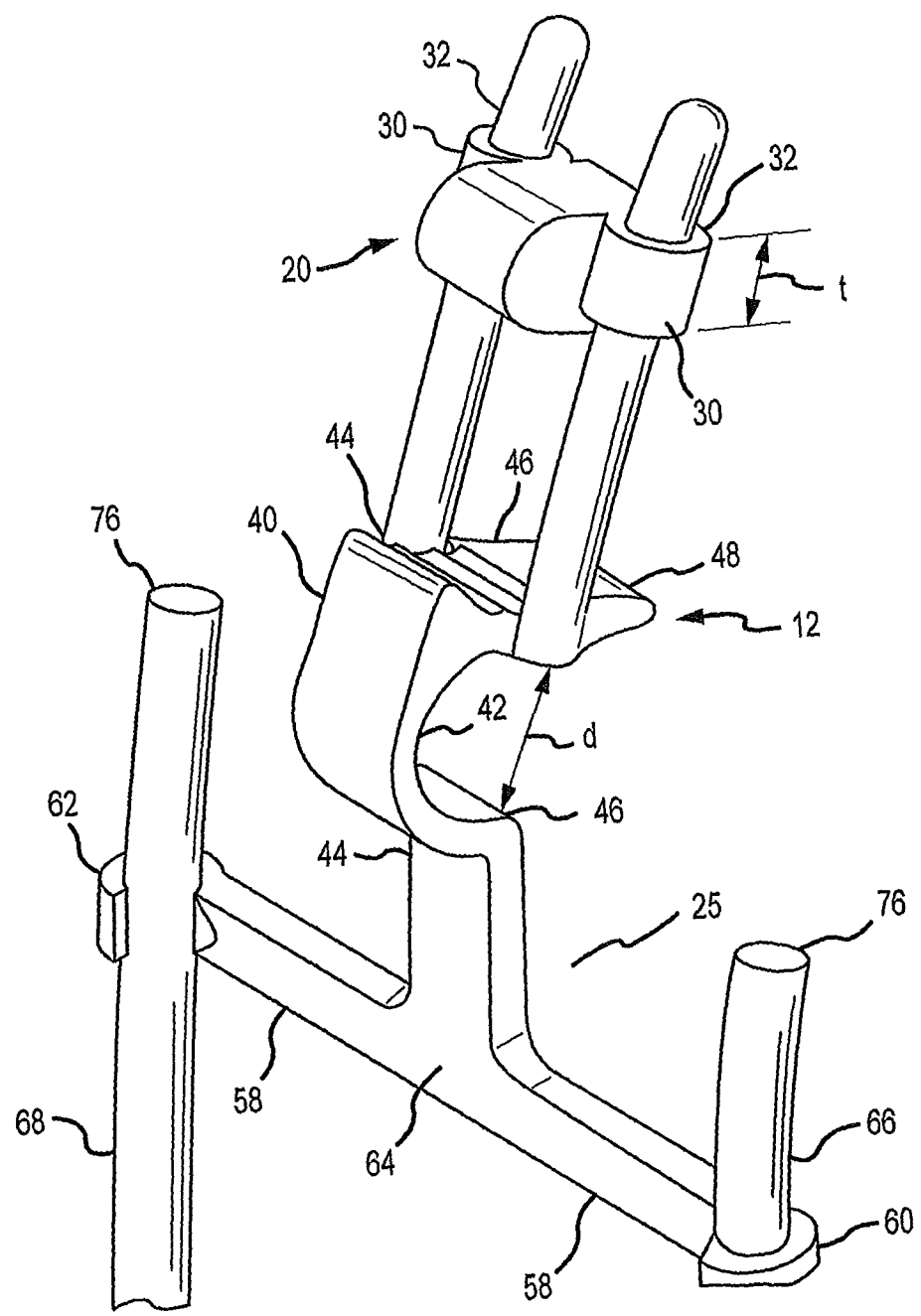
FIG. 9 is an exploded rear perspective view of a portion of the spinal stabilization system shown in FIGS. 6, 7 and 8.
Figure 10:
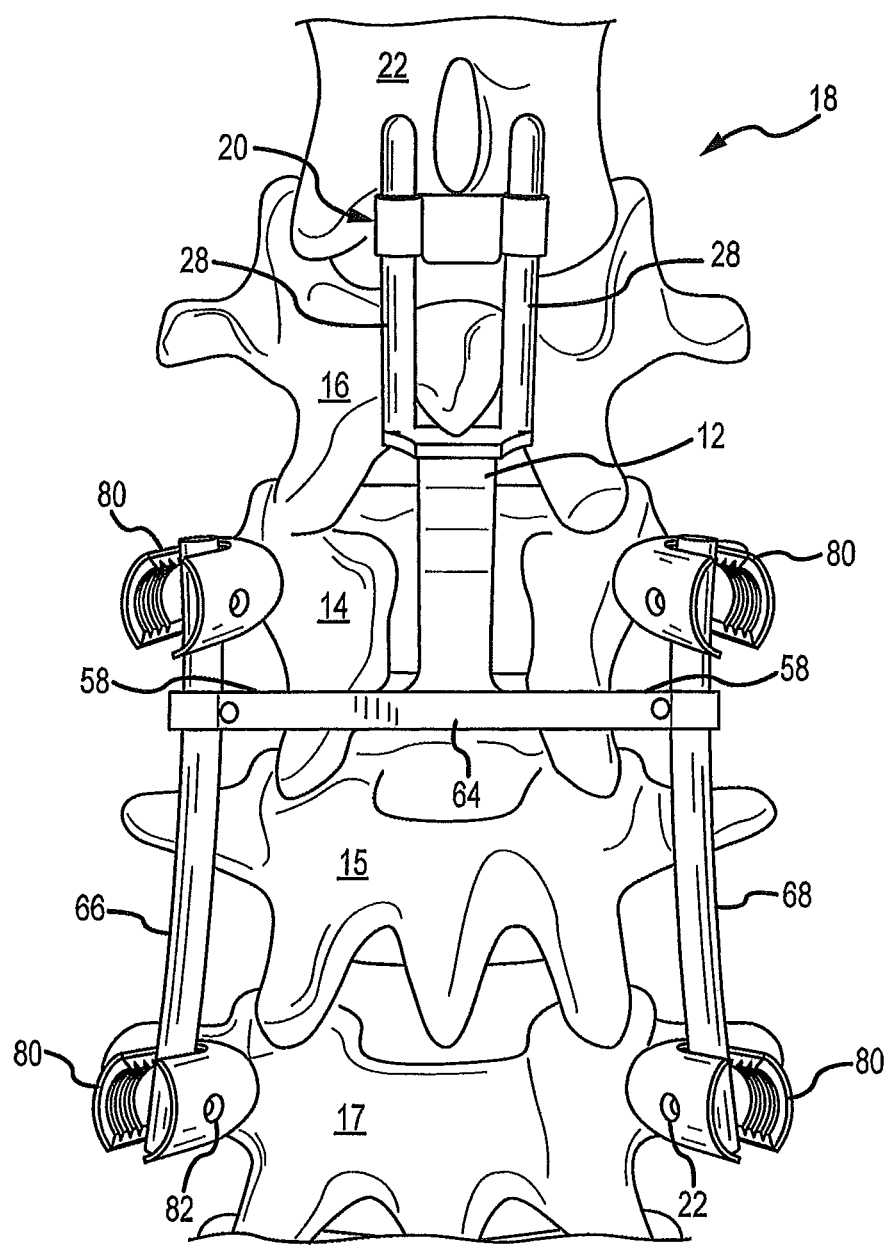
FIG. 10 is a front plan view of a spinal stabilization system of the present invention affixed to a spinal column.
Figure 11:
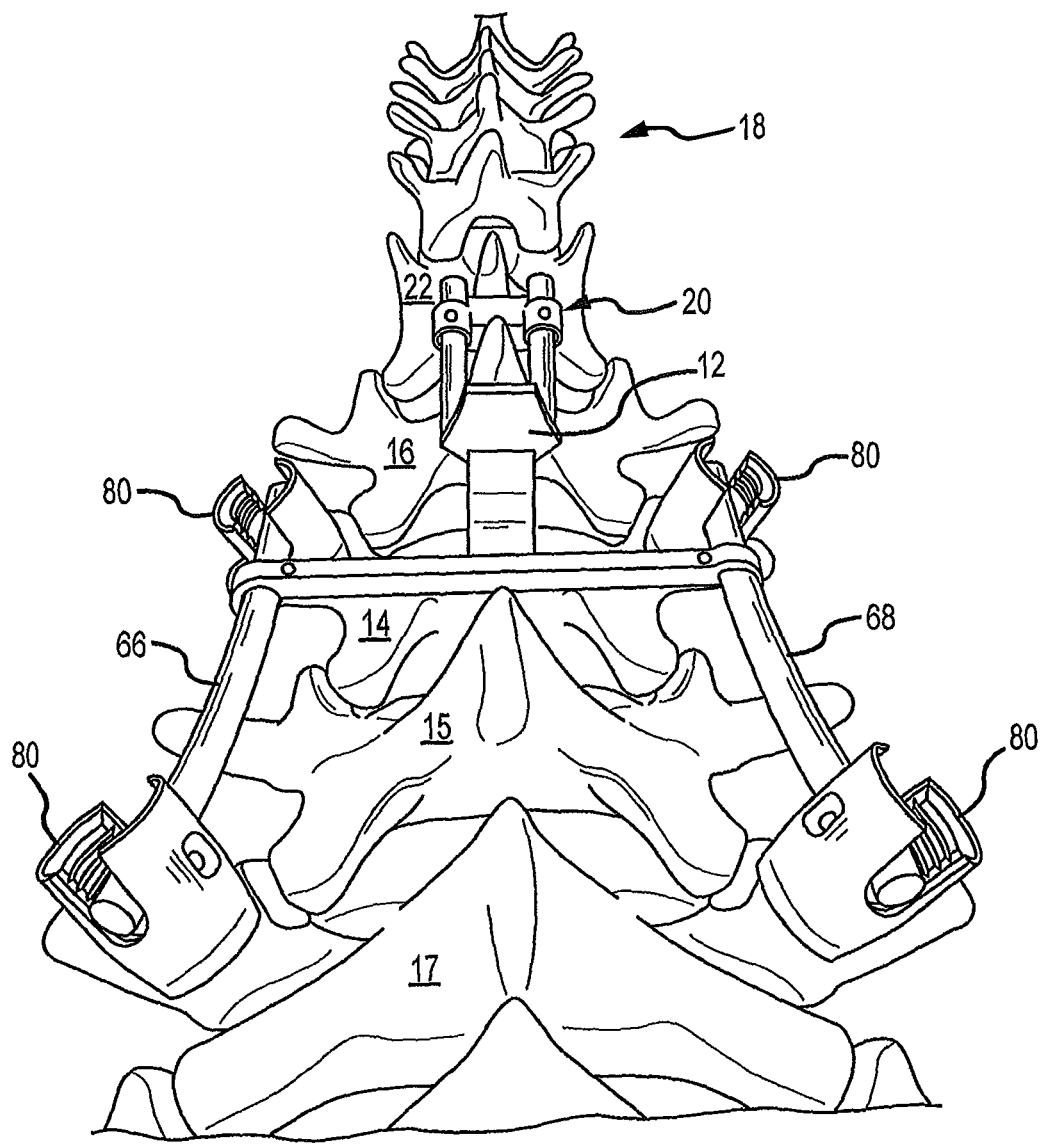
FIG. 11 is a bottom front perspective view of a spinal stabilization system of the present invention affixed to a spinal column.
Figure 12:
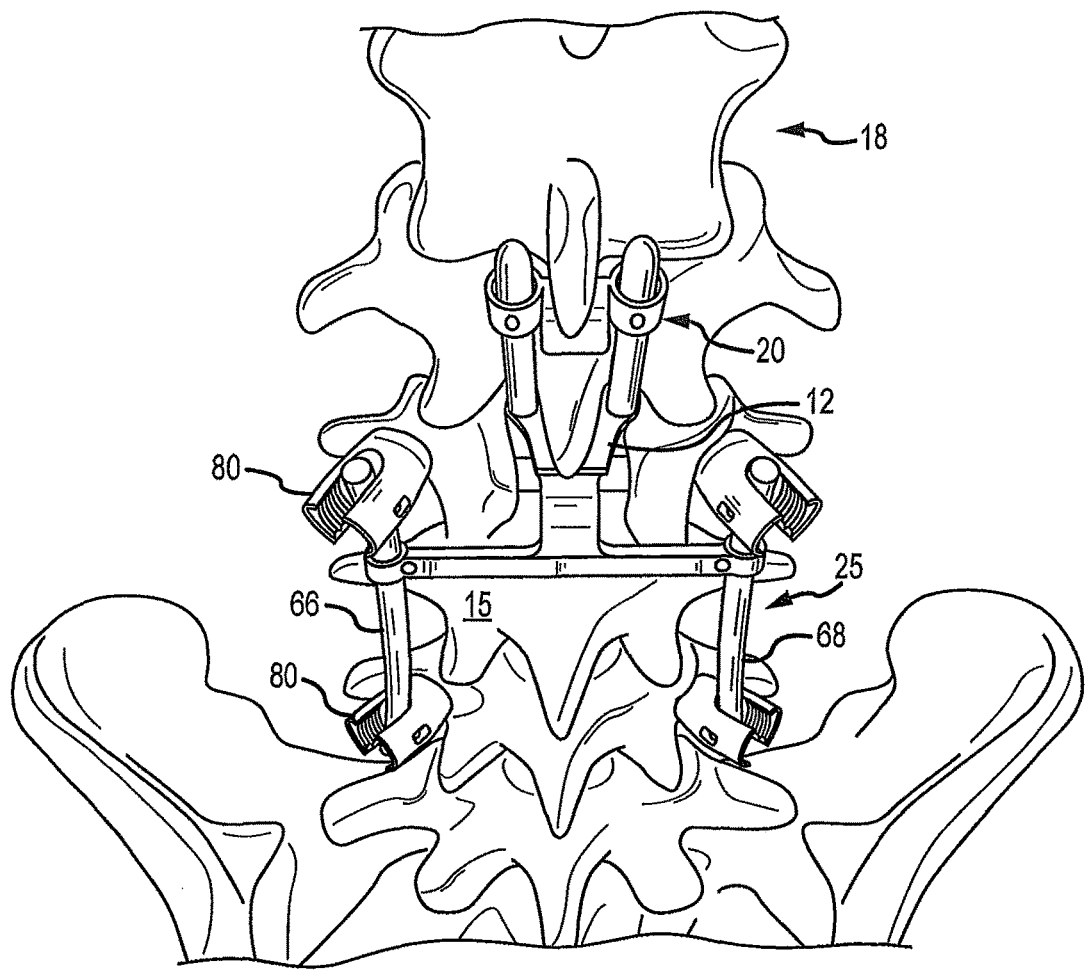
FIG. 12 is a top front perspective view of a spinal stabilization system of the present invention affixed to a spinal column.
Figure 13:
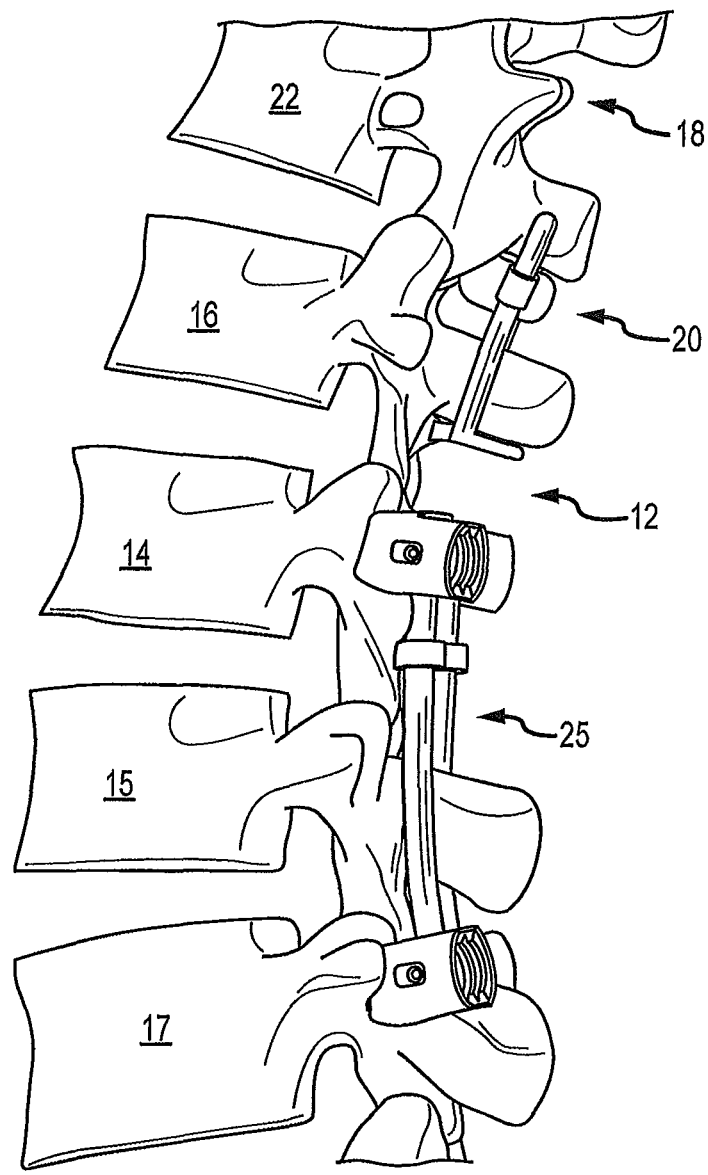
FIG. 13 is a side perspective view of a spinal stabilization system of the present invention affixed to a spinal column.

The support structure 25 comprises a pair of support members or guide rods 28 secured to the first interlaminar support member 12 and extending in a direction upwardly therefrom substantially parallel to one another. The second interlaminar member 20 includes a body portion 21 of a preselected thickness t, which is most clearly illustrated in FIG. 9. Thickness t is selected based upon the spacing between the second and third vertebrae and is intended to be smaller in size than the spacing to allow for flexion of the spinal column 18.

The body portion 21 further includes a pair of oppositely positioned ears 30 extending laterally outwardly from the body portion in opposing directions, each of the ears containing an aperture 32 structured and arranged to slideably receive one of the support members or guide rods 28. As will be discussed in greater detail below, the second interlaminar member is movably supported by upwardly extending support members or guide rods, and the position of the second interlaminar member 20 relative to the first interlaminar member 12 may be adjusted depending upon the dimensions of the specific spinal column on which the system is installed and the range of motion desired. Once the position of the second interlaminar member 20 has been selected, it is locked in place by a pair of set screws or other suitable fastening means 34 extending through each of the ears 30 and adapted to releaseably engage the respective guide rod extending therethrough.

Referring now to FIGS. 2, 3, 7 and 8, the first interlaminar member is 12 depicted in greater detail. The first interlaminar member comprises a U-shaped body 40 defined by an elastic midsection 42, two spaced apart end portions 44, and a pair of juxtaposed legs 46, each leg extending substantially parallel to one another from one of the respective ends in a direction generally outwardly away from the spinal column 18 (FIG. 7) and spaced apart a preselected distance d. Distance d is determined by the size of the first interlaminar member, which, in turn, is selected based upon the spacing between the first and second vertebrae. The first interlaminar member is intended to fuse the first and second vertebrae. Accordingly, it is sized to be a tight fit, and the elastic properties of the U-shaped body 40 act as a spring or shock absorber in the interface between the two vertebrae. Further, the uppermost one of the legs 46 is longer than the lower one of the legs, thereby forming a handle 48 which may be used to insert and position the system during surgery.

Referring again to FIG. 1, the support structure 25 further includes a T-shaped frame member 50 operatively connected to the first and second interlaminar members 12 and 20 and extends generally downwardly therefrom in a direction substantially parallel to the spinal column 18. The T-shaped frame member includes an elongate body 52 having first and second end portions 54, 56, the first end portion being operatively connected to the first interlaminar member 12, and an elongate cross member 58. The cross member has first and second end portions 60, 62 and a midpoint 64 and is structured and arranged to be connected to the second end portion 56 of the body 52 at approximately the midpoint 64. Each of the ends 60, 62 of the cross member 58 are adapted to receive and adjustably secure first and second support members 66 and 68 respectively. In the embodiment shown, each of the end portions 60, 62 have an aperture 70, 72 formed therein respectively for receiving one of the support members 66, 68, each of which may be held in a preselected position by a set screw 74.

In the embodiment shown, by way of example only and not of limitation, the support members are in the form of guide rods 66, 68, each guide rod having an upper end 76 and a lower end 78. Each of the upper and lower ends of the support members 66, 68 has a securing device 80 slideably positioned thereon and adapted to be secured thereto by means of set screws 82. By way of example, each of the securing devices is shown in the form of a pedicle screw 84, each pedicle screw being structured and arranged to be secured to one of the vertebra of the spinal column 18.

Figure 6:
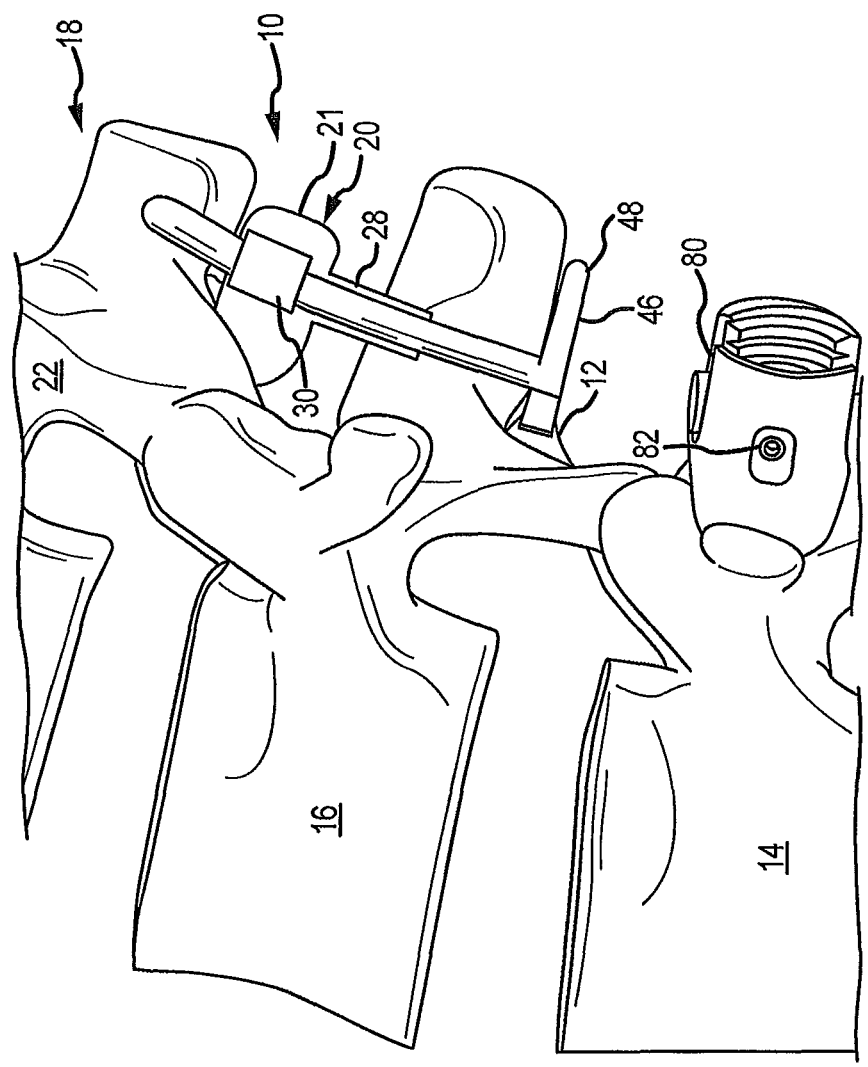
FIG. 6 is an enlarged side plan view of a portion of the spinal stabilization system of the present invention shown in FIG. 3 showing an upper portion of the stabilization system affixed to a spinal column.
Figure 7:
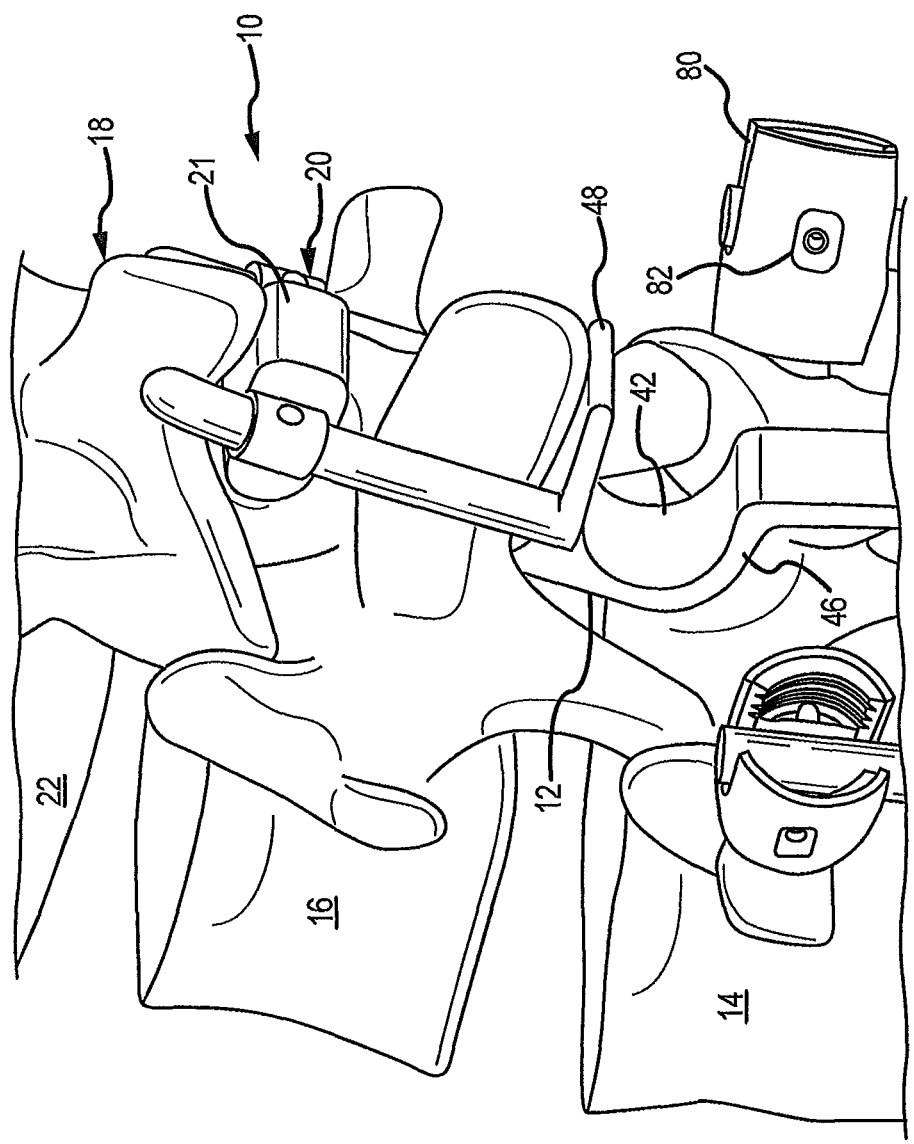
FIG. 7 is a side perspective view of a portion of the spinal stabilization system shown in FIG. 6.
Figure 8:
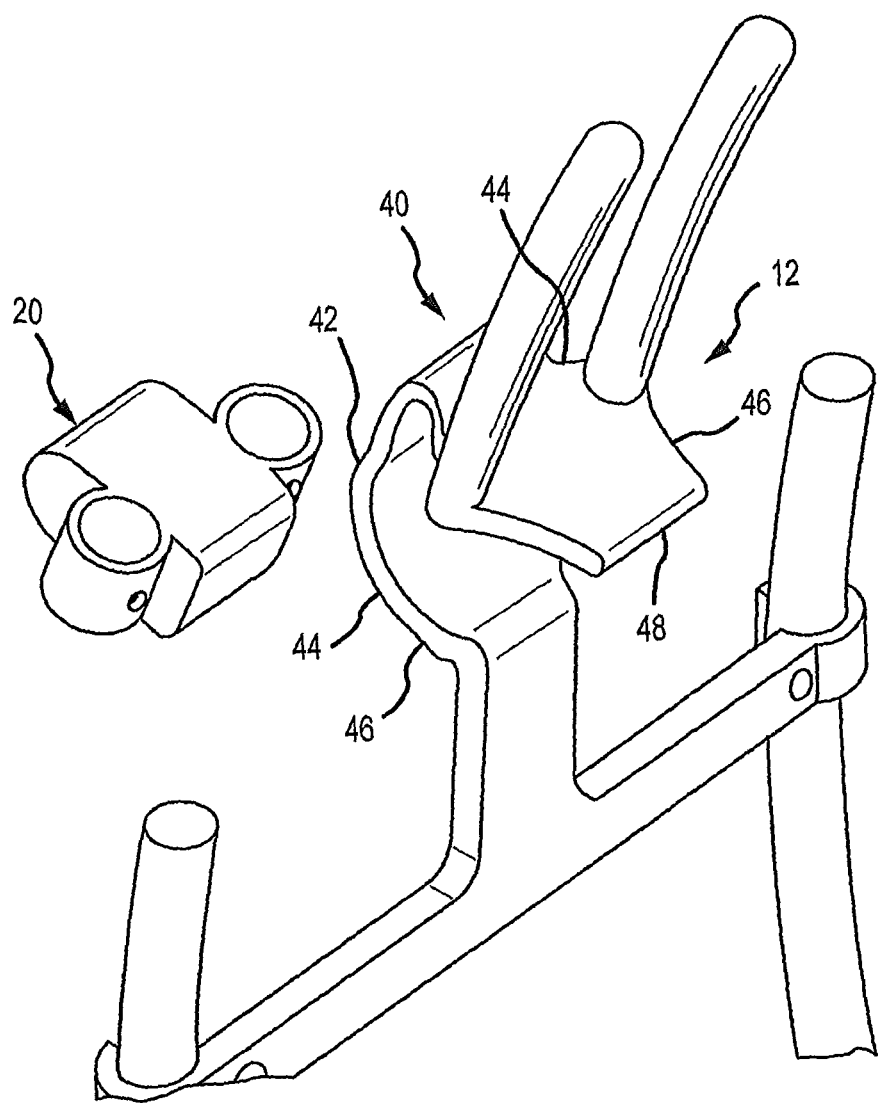
FIG. 8 is an exploded front perspective view of a portion of the spinal stabilization system shown in FIGS. 6 and 7.

The installation and operation of the spinal support system 10 of the present invention are illustrated in greater detail in FIGS. 6, 7, and 10-13. The system advantageously may be installed where other spinal fusion devices or similar medical apparatus are already in place to add stability to the spinal column above and below the installation point, to control flexion and/or rotational movement of the spine or selected vertebrae with respect to one another, and to prevent impingement of adjacent vertebrae, spinal processes, pedicle screws and medical hardware on one another. By way of example, as best shown in FIGS. 6 and 7, a surgeon may insert the system 25 into the space between adjacent vertebrae 14 and 16 by gripping handle 48 and making the insertion. The tight fitting U-shaped body 40 not only serves to control any motion between the adjacent vertebrae or even eliminate it entirely, thereby effectively fusing the vertebrae, but also serves as a dampening cushion or spring device by virtue of the spring-like elasticity of the body 40 translated to the vertebrae via legs 46. Thereafter, the second interlaminar member 20 may be selectively positioned intermediate vertebra 16 and vertebra 22 to permit flexion on a forward direction but to limit extension in the rearward direction and to limit compression of the spinal segment, thereby imparting enhanced stability to the spinal column above the fused vertebrae.

In a similar manner, support structure 25, via the T-shaped frame member 50 and support members or guide rods 66 and 68, provides support to the spinal processes located below the fused vertebrae 14 and 16. As shown in FIGS. 10-13, the pedicle screws 80 may be positioned in first vertebra 14 and in either vertebra 15 immediately adjacent to vertebra 14, or at a lower level as shown by vertebra 17, thus extending the stabilizing effect of the novel support system of the present invention to multiple levels in the spinal column 18. More than one level may be addressed simply by lengthening the rods 66 and 68 and slideably positioning multiple pedicle screws 80 thereon for selective positioning along the spinal column.

In one aspect, the cross member midpoint 64 may be configured, structured and arranged to be adjustably (e.g., pivotably or translatably) connected or secured to the second end portion 56 of the body 52 at approximately the midpoint 64 in order to allow a surgeon during the course of the surgical procedure to adjust and align components of the implant in relation to the patient's bony anatomy and in relation to support members 66 and 68.

In another aspect, elongate body 52 may be comprised of multiple pieces. For example, one or more linear racks may be configured in operable relation with gear mechanisms, thereby forming a ratchet device (not shown), in order to extend the distance between first and second end portions 54 and 56 thereby permitting a surgeon during the course of the surgical procedure to adjust and align components of the implant in relation to the patient's bony anatomy and subsequently securing them in place. For example, a ratchet mechanism configuration may permit the surgeon to progressively extend elements of the implant to better appose a lamina.

In yet another aspect, each of the ends 60, 62 of the cross member 58 may be configured to permit a degree of adjustability (e.g., pivotably or translatably) to receive and adjustably secure first and second support members 66 and 68 respectively. For example any cross-link variable adjustment mechanism or fastener known in the art may be employed to accomplish the desired fixation between the ends 60, 62 of the cross member 58 and first and second support members 66 and 68.

According to particular embodiments, interlaminar member 20 may be configured to permit connection to guide rods 28 via an approach that is substantially perpendicular to the longitudinal axis of guide rods 28. In other words, after the other components of the system have been implanted via a posterior approach to the posterior aspect of the spine the interlaminar member 20 may follow a generally similar approach trajectory and then secured to the guide rods 28 with, e.g., set screws in a similar manner to the engagement between the ends 60, 62 of the cross member 58 and first and second support members 66 and 68. Furthermore, in another aspect, an interlaminar member 20 may be used alone (and may alternatively be configured to be similar to the U-shaped body 40) and may be directly engaged with a first and second support members 66 and 68 and positioned between the lamina and spinous processes of the spine.

In particular aspects, the different elements of the system may be configured with tool engagement features in order to permit a surgeon to grasp the implant with a tool assembly or insertion tool to ease implantation of the various components. For example, the insertion tool may be configured as a pair of pliers or hemostats. As another example, a threaded portion of a tool assembly may reversibly secure to a complementary threaded portion of the implant in order to ease implantation. E.g., a tool assembly may be comprised of a cannulated shaft with a retainer shaft housed substantially within, the retainer shaft further configured with a threaded portion at its distal end which may extend out of a distal end of the retainer shaft and a handle located and attached to a proximal end of the retainer shaft; the distal end of the retainer shaft may have a feature that permits rotation of the retainer shaft via another tool, such as the mechanical arrangement that exists between a wrench and nut, in order to secure the tool assembly to the implant. After implantation of the implant the tool assembly may be decoupled and removed.

Changes may be made in the above methods and systems without departing from the scope hereof. It should thus be noted that the matter contained in the above description and/or shown in the accompanying figures should be interpreted as illustrative and not in a limiting sense. The following claims are intended to cover all generic and specific features described herein, as well as all statements of the scope of the present systems and methods, which, as a matter of language, might be said to fall there between.

What is claimed is:

1. A method of treating a patient's spinal column, the patient having a bony anatomy including a spinal column comprising a plurality of operatively interconnected vertebrae, each of the plurality of vertebrae being positioned at a certain level in the spinal column and being separated from an adjacent one of the plurality of operatively interconnected vertebrae by an interlaminar space or spacing located therebetween, the method comprising:

a. positioning a spinal stabilization system along the patient's spinal column, the spinal stabilization system including:
   a first interlaminar member adapted to be positioned between a first one of the plurality of vertebrae and a second one of the plurality of vertebrae in the spinal column; the first interlaminar member including a U-shaped body having a midsection, two spaced apart end portions, and a pair of juxtaposed legs extending substantially parallel to one another from one of the respective ends in a direction generally outwardly away from the spinal column and spaced apart a preselected distance, d;
   a support structure operatively connected to the first interlaminar member, the support structure including a T-shaped frame member operatively connected to the first interlaminar member and extending generally downwardly therefrom in a direction substantially parallel to the spinal column, the T-shaped frame member including an elongate body having first and second end portions, the first end portion being operatively connected to the first interlaminar member, and an elongate cross member having first and second end portions and a midpoint, the elongate cross member being operatively connected approximately at the midpoint to the second end portion of the elongate body;
   a pair of support members secured to the first interlaminar member extending upwardly therefrom in a direction substantially parallel to one another; and
   a second interlaminar member, the second interlaminar member being operatively connected to the pair of support members and adapted to be positioned between the second one of the plurality of vertebrae and a third one of the plurality of vertebrae positioned adjacent to the second one of the plurality of vertebrae in the spinal column;
b. inserting the first interlaminar member into the spacing between the first one and the second one of the plurality of operatively interconnected vertebrae;
c. determining the spacing between the second and the third one of the plurality of operatively interconnected vertebrae;
d. selectively sizing the second interlaminar member in response to the spacing between the second and the third one of the plurality of operatively interconnected vertebrae whereby motion therebetween may be selectively controlled;
e. adjustably positioning the second interlaminar member on the pair of support members extending upwardly from the first interlaminar member whereby the second interlaminar member is aligned with the spacing between the second and the third one of the plurality of operatively interconnected vertebrae;
f. inserting the second interlaminar member into the spacing between the second one and the third one of the plurality of operatively interconnected vertebrae;
g. adjusting and aligning the spinal stabilization system in relation to the patient's bony anatomy; and
h. securing the spinal stabilization structure to the patient's spinal column.

2. The method of claim 1, further comprising, prior to step b.:
   a. determining the spacing between the first and the second one of the plurality of operatively interconnected vertebrae; and,
   b. selectively sizing the first interlaminar member in response to the spacing between the first and the second one of the plurality of operatively interconnected vertebrae whereby motion therebetween may be selectively controlled.

3. The method of claim 2 wherein the step of selectively sizing the first interlaminar member includes selecting the distance d between the pair of juxtaposed legs so that the first interlaminar member is sized to be a tight fit in the spacing between the first one and the second one of the plurality of operatively interconnected vertebrae, whereby the first one and the second one of the plurality of operatively interconnected vertebrae are fused.

4. The method of claim 2 wherein the step of adjusting and aligning the spinal stabilization system includes the step of positioning the first interlaminar member in the spacing between the first one and the second one of the plurality of operatively interconnected vertebrae whereby a top surface of one of the pair of juxtaposed legs is in contact with a surface of a spinous process of the second vertebra.

5. The method of claim 3 wherein the U-shaped body is structured and arranged to have preselected elastic properties and wherein the step of selectively sizing the first interlaminar member further includes the step of selecting the elastic properties of the U-shaped body such that the U-shaped body serves as a spring or as a shock absorber in the spacing between the first one and the second one of the plurality of operatively interconnected vertebrae.

6. The method of claim 1 wherein an uppermost leg of the pair of juxtaposed legs of the U-shaped body is longer than a lower leg of the pair of juxtaposed legs, thereby forming a handle structured and arranged to be used to insert and position the spinal stabilization system, the step of inserting the first interlaminar member into the spacing between the first one and the second one of the plurality of operatively interconnected vertebrae further including the step of using the handle to insert and position the system during surgery.

7. The method of claim 1 wherein the step of adjustably positioning the second interlaminar member on the pair of support members extending upwardly from the first interlaminar member further includes the step positioning the second interlaminar member on the pair of support members via an approach that is substantially perpendicular to a longitudinal axis of the pair of support members.

8. The method of claim 1 wherein the step of adjusting and aligning the spinal stabilization system in relation to the patient's bony anatomy further includes selectively adjusting a position of the second interlaminar member relative to a position of the first interlaminar member.

9. The method of claim 1 wherein the step of inserting the second interlaminar member into the spacing between the second one and the third one of the plurality of operatively interconnected vertebrae further includes selectively positioning the second interlaminar member intermediate the second one of the plurality of vertebrae and third one of the plurality of vertebrae such that i) a substantial gap is formed between the second interlaminar member and a surface of a spinous process of the second one of the plurality of vertebrae and ii) the second interlaminar member is positioned immediately adjacent a surface of a spinous process of the third one of the plurality of vertebrae thereby providing a preselected amount of flexion of the vertebra on a forward direction and limiting extension of the vertebra in a rearward direction.

10. The method of claim 8 wherein the step of adjusting and aligning the spinal stabilization system further includes selectively positioning the second interlaminar member intermediate the second one of the plurality of vertebrae and third one of the plurality of vertebrae such that i) a substantial gap is formed between the second interlaminar member and a surface of a spinous process of the second one of the plurality of vertebrae and ii) the second interlaminar member is positioned immediately adjacent a surface of a spinous process of the third one of the plurality of vertebrae thereby providing a preselected amount of flexion of the vertebra on a forward direction and limiting extension of the vertebra in a rearward direction.

11. The method of claim 1 wherein the first and second end portions of the elongate cross member are each adapted to receive and adjustably secure an elongate support member therein, the method further including the step of inserting an elongate support member in each of the first and second ends of the elongate cross member respectively.

12. The method of claim 11 wherein each of the elongate support members includes an upper end, a lower end and a length extending therebetween, each elongate support member being structured and arranged to slideably receive a securing device thereon, the method further including positioning a securing device along the respective first and second lengths of each of the elongate support members.

13. The method of claim 12 wherein each of the securing devices is adapted to receive a pedicle screw therein, each pedicle screw being adapted to be secured to one of the plurality of operatively interconnected vertebrae, the method including the step of positioning a pedicle screw in each of the securing devices.

14. The method of claim 13 further including the step of securing each of the pedicle screws to one of the plurality of vertebrae of the patient's spinal column.

15. The method of claim 14 including the step of readjusting and realigning the spinal stabilization system in relation to the patient's bony anatomy.

16. The method of claim 15 further including the step of securing each of the pedicle screws in the securing device in which it is positioned.

17. The method of claim 15 further including the step of selectively lengthening at least one of the elongate support members whereby a stabilizing effect of the spinal stabilization system is extended to multiple levels in the spinal column.

18. The method of claim 17 further including the step of slideably positioning multiple pedicle screws on the at least one of the elongate support members.

19. The method of claim 1, wherein the U-shaped body comprises a protuberance at a location at or near a first end portion comprising the two spaced apart end portions of the U-shaped body, the protuberance extending away from the U-shaped body in a particular direction such that when positioned up to the spinal column the protuberance abuts a lamina of the second vertebra.

20. The method of claim 7, wherein the second interlaminar member comprises a U-shaped body.

* * * * *